(12) United States Patent
Jung et al.

(10) Patent No.: US 10,092,873 B2
(45) Date of Patent: Oct. 9, 2018

(54) AIR CLEANING SYSTEM AND METHOD OF CONTROLLING THE SAME

(71) Applicant: LG ELECTRONICS INC., Seoul (KR)

(72) Inventors: Yeekyeong Jung, Seoul (KR); Chulwoo Park, Seoul (KR); Sunghwa Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 104 days.

(21) Appl. No.: 15/120,479

(22) PCT Filed: Dec. 12, 2014

(86) PCT No.: PCT/KR2014/012277
§ 371 (c)(1),
(2) Date: Aug. 19, 2016

(87) PCT Pub. No.: WO2015/130001
PCT Pub. Date: Sep. 3, 2015

(65) Prior Publication Data
US 2017/0065922 A1 Mar. 9, 2017

(30) Foreign Application Priority Data
Feb. 27, 2014 (KR) .................. 10-2014-0023205

(51) Int. Cl.
*B01D 46/00* (2006.01)
*B01D 46/44* (2006.01)
(Continued)

(52) U.S. Cl.
CPC .............. *B01D 46/442* (2013.01); *A61L 9/00* (2013.01); *B01D 46/0028* (2013.01);
(Continued)

(58) Field of Classification Search
CPC ............ B01D 46/0024; B01D 46/0028; B01D 51/00; B01D 50/00; B01D 27/08;
(Continued)

(56) References Cited

U.S. PATENT DOCUMENTS

| 6,716,406 B2* | 4/2004 | Reisfeld ................ A61L 9/20 423/245.1 |
| 2010/0150787 A1* | 6/2010 | Choi .................. B01D 46/0028 422/122 |

(Continued)

FOREIGN PATENT DOCUMENTS

| CN | 101806486 A | 8/2010 |
| CN | 102154096 A | 8/2011 |

(Continued)

OTHER PUBLICATIONS

International Search Report from PCT/KR2014/012277, dated Mar. 24, 2015.

*Primary Examiner* — Duane Smith
*Assistant Examiner* — Minh-Chau Pham
(74) *Attorney, Agent, or Firm* — Dentons US LLP

(57) ABSTRACT

An air cleaning system and a method of controlling the same, the air cleaning system including a particle separation device for suctioning indoor air to separate microbial particles from air particles, a collection device collecting the microbial particles separated by the particle separation device, a luminescence measurement device for detecting an amount or intensity of light emitted from the microbial particles collected in the collection device, and at least one air cleaning device that selectively operates on the basis of contamination of the microbial particles detected by the luminescence measurement device.

20 Claims, 6 Drawing Sheets

(51) Int. Cl.
*F24F 3/16* (2006.01)
*A61L 9/00* (2006.01)
*B01D 46/42* (2006.01)
*B01D 46/48* (2006.01)
*F24F 110/66* (2018.01)
*F24F 11/39* (2018.01)

(52) U.S. Cl.
CPC ..... *B01D 46/0056* (2013.01); *B01D 46/4263* (2013.01); *B01D 46/48* (2013.01); *F24F 3/16* (2013.01); *A61L 2209/14* (2013.01); *F24F 11/39* (2018.01); *F24F 2110/66* (2018.01); *Y02A 50/249* (2018.01); *Y02B 30/78* (2013.01)

(58) Field of Classification Search
CPC ... B01J 8/00; B03C 3/011; B03C 3/36; B03C 3/016; B03C 3/38
USPC .......... 55/358, 344, 472, 473; 96/16, 55, 63, 96/64, 224, 397; 95/8, 12; 422/108, 110, 422/122, 186.3; 423/245.1
See application file for complete search history.

(56) References Cited

U.S. PATENT DOCUMENTS

| | | | |
|---|---|---|---|
| 2011/0100221 A1* | 5/2011 | Wu | B01D 46/0024 96/16 |
| 2011/0183371 A1 | 7/2011 | Noda et al. | |
| 2016/0131623 A1* | 5/2016 | Morgan | G01N 33/0004 250/338.5 |

FOREIGN PATENT DOCUMENTS

| | | | | |
|---|---|---|---|---|
| EP | 2505990 A1 * | 10/2012 | | G01N 21/76 |
| JP | 2004-301387 A | 10/2004 | | |
| JP | 2011-21931 A | 2/2011 | | |
| JP | 2012-46318 A | 3/2012 | | |
| KR | 10-0813679 B1 | 3/2008 | | |
| KR | 10-2011-0128600 A | 11/2011 | | |
| WO | 02/088673 A2 | 11/2002 | | |

* cited by examiner

[Fig. 1]
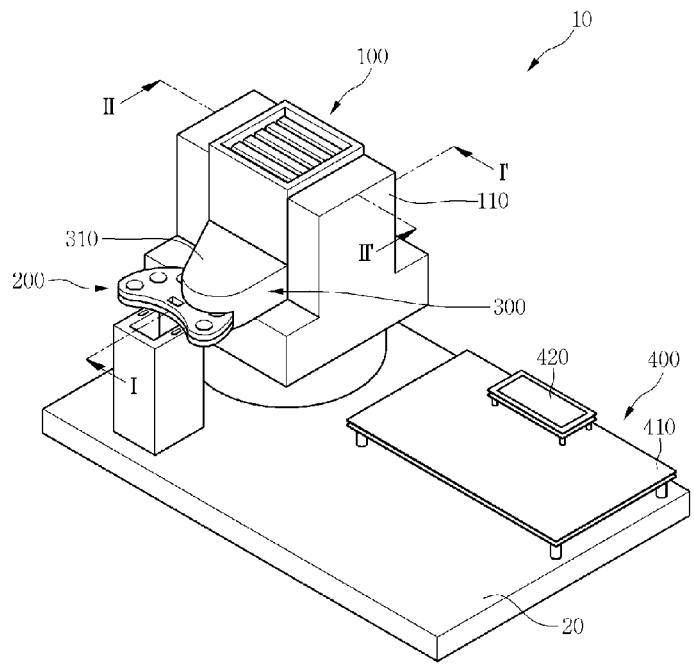
[Fig. 2]
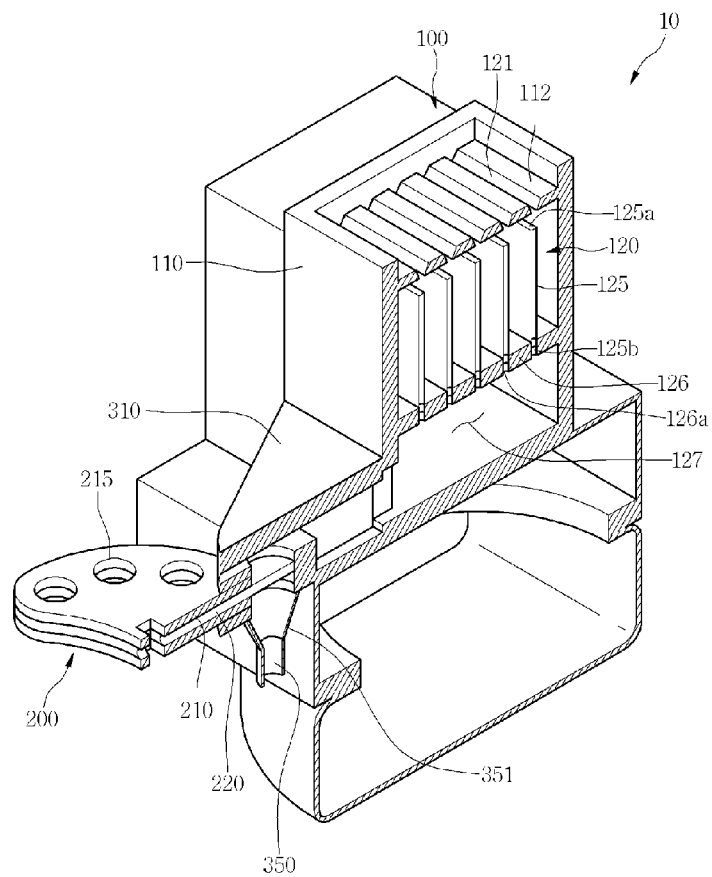

[Fig. 3]
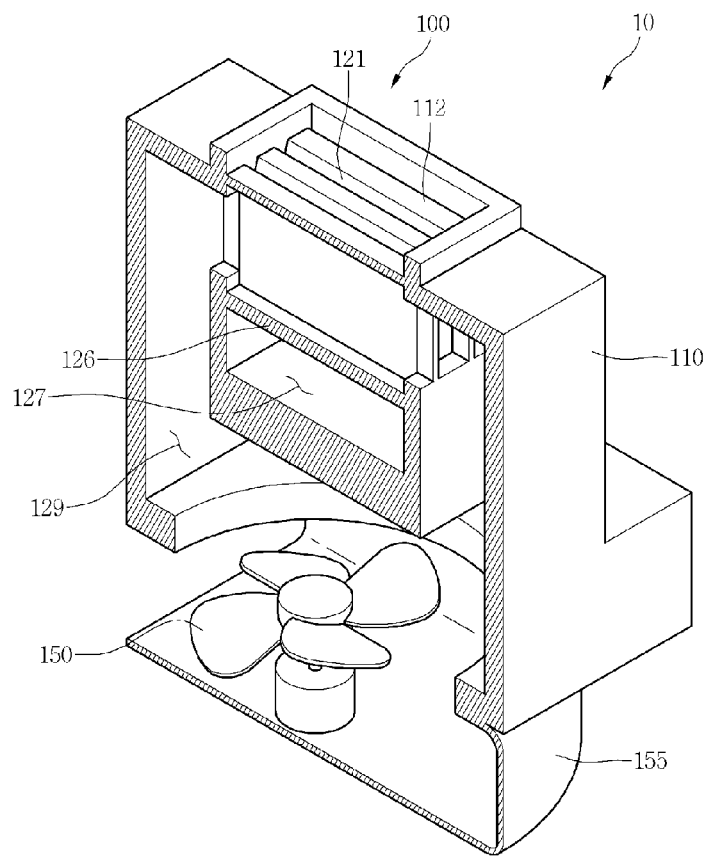
[Fig. 4]
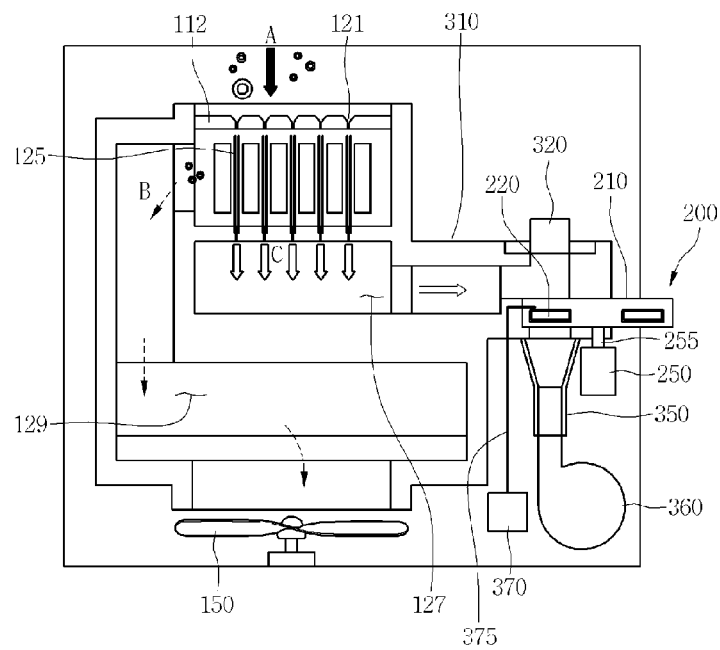

[Fig. 5]
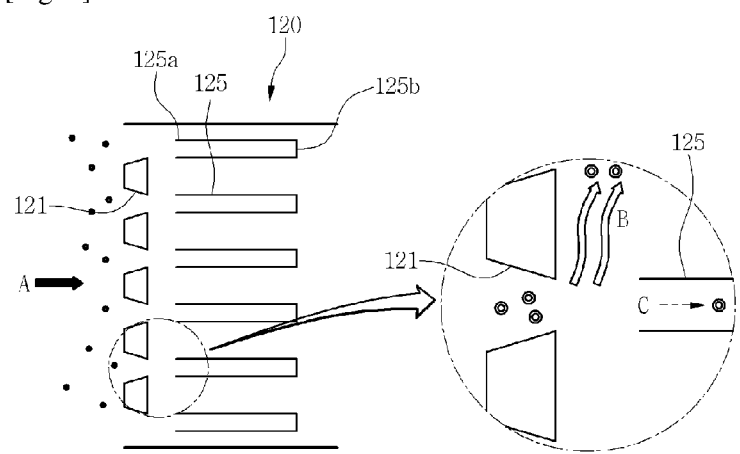
[Fig. 6]
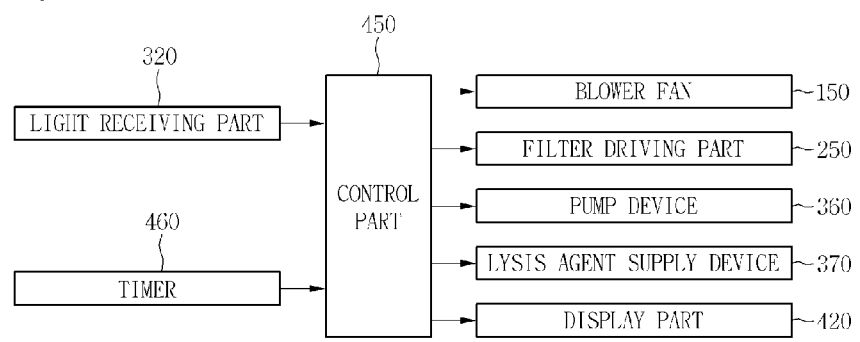

[Fig. 7]
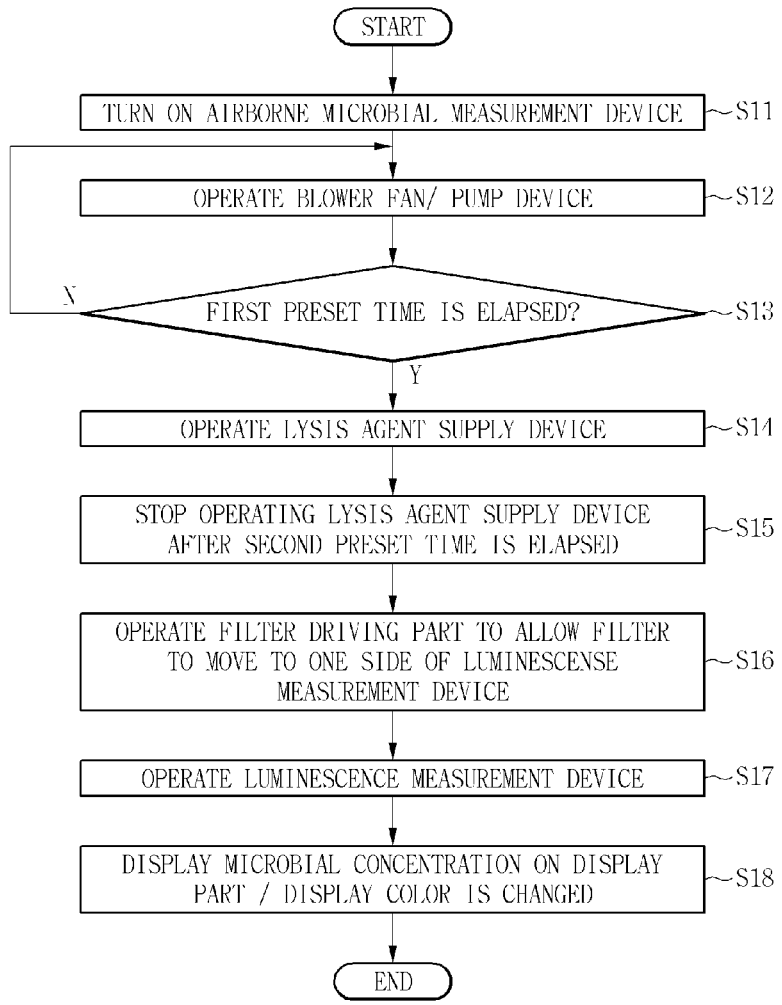

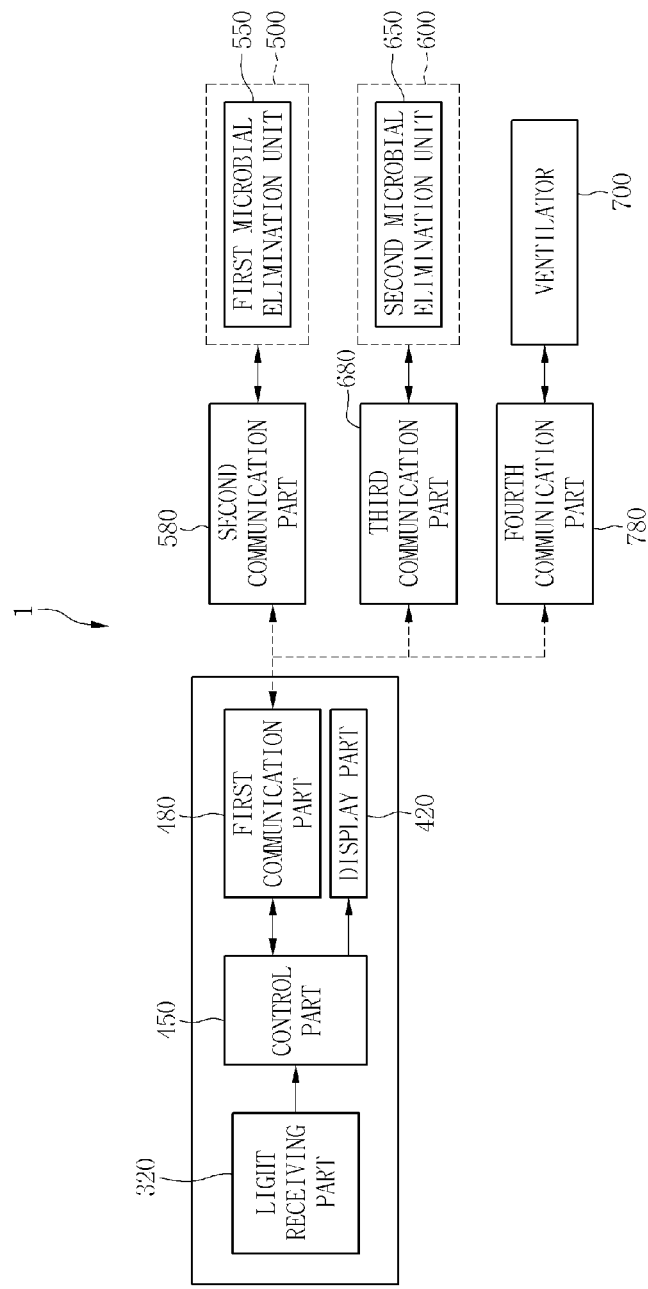
[Fig. 8]

[Fig. 9]
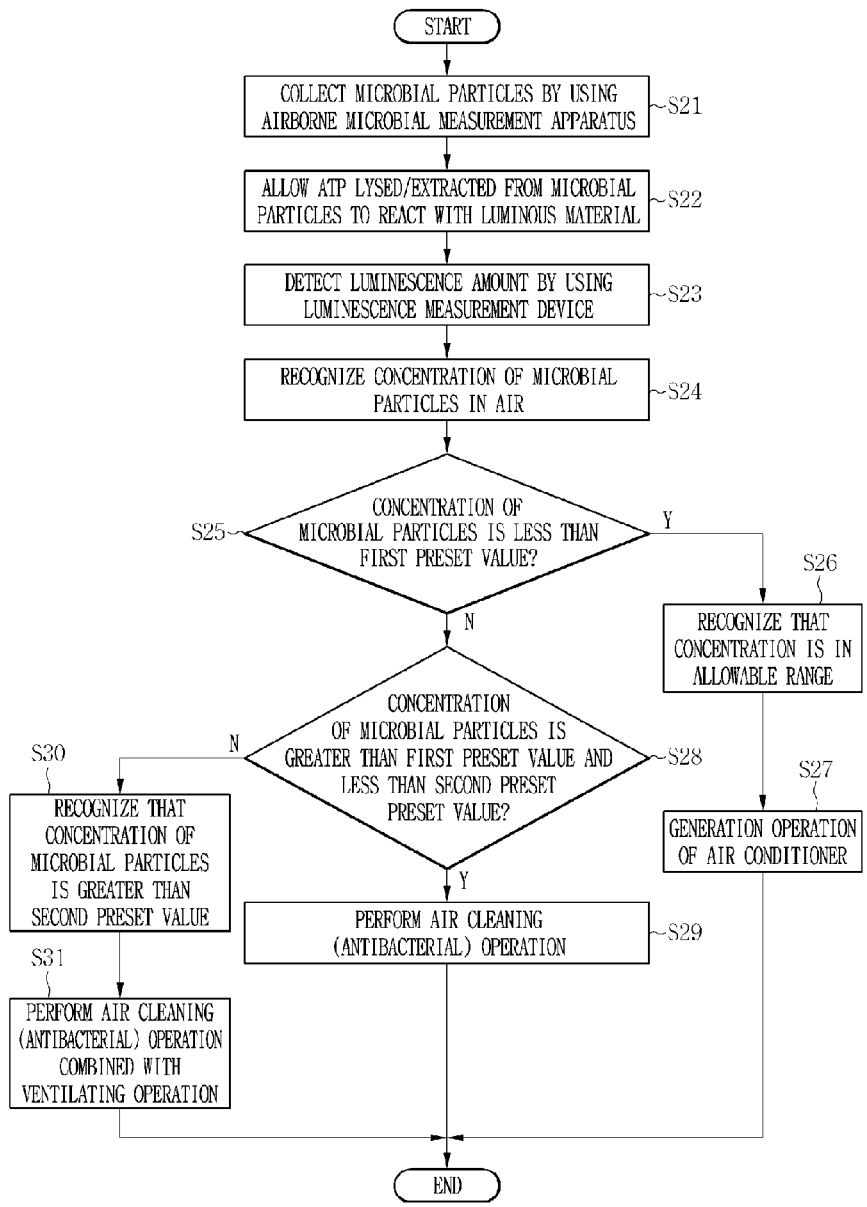
[Fig. 10]
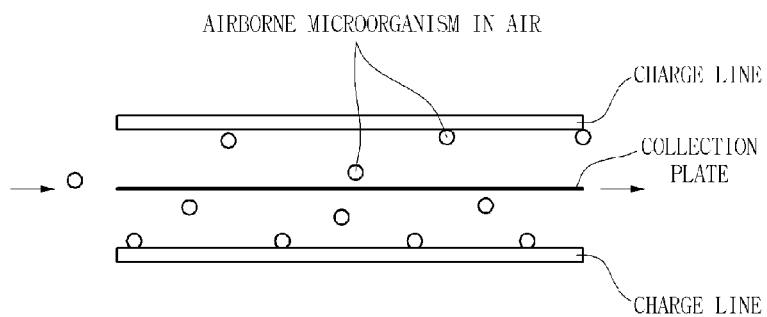

AIR CLEANING SYSTEM AND METHOD OF CONTROLLING THE SAME

This application is a National Stage Application of International Application No. PCT/KR2014/012277, filed on Dec. 12, 2014, which claims the benefit of Korean Patent Application No. 10-2014-0023205, filed on Feb. 27, 2014, all of which are hereby incorporated by reference in their entirety for all purposes as if fully set forth herein.

TECHNICAL FIELD

The present disclosure relates to an airborne microbial measurement apparatus and method.

BACKGROUND ART

In recent years, as avian influenza and new type influenza are issued, aerial infection problems are becoming the main issue of society. For this reason, the subject with regard to a method of measuring airborne microbial particles in air is importantly treated, and a biosensor market is sharply growing accordingly.

As the existing method of measuring airborne microbial particles in air, there are a culture method in which airborne bioparticles in a sample gas are collected onto a surface of a solid or liquid suitable for growth to culture the collected bioparticles under an appropriate temperature-humidity condition for a predetermine time, thereby calculating the number of collected microorganism from the number of colony generated on the surface and a staining method in which bioparticles are stained to measure the number of microorganism by using a fluorescence microscope.

Recently, an adenosine triphosphate (ATP) bioluminescence method using a principle in which ATP reacts with luciferin/luciferase to emit light may be developed to allow a series of processes including ATP elimination process, ATP extraction, and luminescence amount measurement to be performed within about thirty minutes, thereby implementing rapid working.

However, according to the above-described methods, the airborne microbial particles existing in the air may not be measured in real time, and a series of handworks including a separate sampling process and pretreatment process is required. Thus, there is a limitation in that a system of automatically measuring the airborne microbial particles in the air can not be developed by using these methods.

FIG. 10 is a view of an electric dust collector provided in an airborne microbial measurement apparatus according to a related art.

Referring to FIG. 10, an electric dust collector according to the related art includes collection plates disposed on both sides thereof and a charge line (a discharge electrode) disposed between the collection plates disposed on both sides thereof.

When a high voltage is applied to the charge line, corona discharge occurs to generate ions. Here, predetermined particles in a gas are charged by the generated ions. Also, the charged particles may move and be collected to a dust collection electrode (the collection plate) by an electric force. That is, the electric dust collector may be understood as a dust collecting device that is capable of collecting predetermined particles using an electrostatic principle. The predetermined particles may include foreign substances such as dusts or airborne microorganism.

The airborne microbial measurement apparatus according to the related art includes the electric dust collector and a collection rod for collecting the microorganism collected onto the collection plate. In the airborne microbial measurement apparatus according to the related art, when the airborne microorganism is collected onto the collection plate by driving of the electric dust collector, a user manually put the collection rod into contact with the collection plate to collect or sample the airborne microorganism. Also, the collected airborne microorganism reacts with a lysis reagent to emit light. Here, the measurement apparatus detects the emitted light to measure a concentration of the microorganism.

Like this, in the case of the airborne microbial measurement apparatus according to the related art, since the collection rod has to be separately provided, and also the user has to collect the airborne microorganism collected onto the collection plate by using the collection rod, it takes a lot of time and also comes expensive.

A system that detects the concentration of the microorganism in the air and is interlocked with an air cleaning device according to the detected microbial concentration does not have been provided in the related art. Therefore, when the air is contaminated, there is a limitation in that an air cleaning or antibacterial operation is limited.

DISCLOSURE OF INVENTION

Technical Problem

Embodiments provide an air cleaning system that measures airborne microorganism existing in air to efficiently operate according to the measured microbial concentration and a method for controlling the same.

Solution to Problem

In one embodiment, an air cleaning system includes: a particle separation device for suctioning indoor air to separate microbial particles from air particles; a collection device collecting the microbial particles separated by the particle separation device; a luminescence measurement device for detecting an amount or intensity of light emitted from the microbial particles collected in the collection device; and at least one air cleaning device that selectively operates on the basis of contamination of the microbial particles detected by the luminescence measurement device.

The air cleaning device may include at least one of: an air conditioner for cooling or heating an indoor space and cleaning the indoor air; an air cleaner for cleaning the indoor air; and a ventilator for ventilating the indoor space by exchanging the indoor air with outdoor air.

In the air conditioner or the air cleaner, a filter member for filtering the microbial particles or an ion generator for generating ions to eliminate the microbial particles may be disposed to perform the indoor air cleaning operation.

When the concentration of the microbial particles is greater than a preset value, one of the air conditioner and the air cleaner may perform the indoor air cleaning operation.

When the concentration of the microbial particles is in ranging from the first preset value to a second preset value, while the air conditioner operates, the air conditioner may perform the indoor air cleaning operation, and when the air conditioner does not operate, the air cleaner may perform the indoor air cleaning operation.

When the concentration of the microbial particles is greater than a second preset value, while the air conditioner operates, the ventilator may operate, and the air conditioner may perform the indoor air cleaning operation, and when the air conditioner does not operate, the ventilator may operate, and the air cleaner may perform the indoor air cleaning operation.

The particle separation device may further include: a pump unit for generating a flow of the microbial particles; and a blower fan for generating a flow of the air particles.

The particle separation device may include: an introduction part for introducing the indoor air; and a nozzle part disposed at one side of the introduction part, wherein the nozzle part may include: an inlet spaced apart from the introduction part in one direction to introduce the microbial particles; and an outlet discharging the microbial particles toward the collection device.

The collection device may include: a filter part for collecting the microbial particles; a filter case accommodating the filter part; and a plurality of filter holes defined in the filter case to communicate with a microbial particle passage.

The air cleaning system may further include a filter driving part for rotating the filter part or the filter case, wherein, when the filter driving part operates in the state where the microbial particles are collected onto the filter part through one of the plurality of filter holes, the other one of the plurality of filter holes may move to a position where the microbial particles are collectible.

The air cleaning system may further include: a lysis agent supply device for supplying lysis reagent into the filter part; and a luminous material disposed in the filter part.

In another embodiment, a method of controlling an air cleaning system includes: separating microbial particles and air particles from indoor air; collecting the separated microbial particles onto a filter part; supplying a lysis reagent into the filter part to extract adenosine triphosphate (ATP) of the microbial particles, wherein the extracted ATP reacts with a luminous material; detecting an amount or intensity of light emitted by the reaction to recognize concentration of the microbial particles; and selectively driving one or more air cleaning devices on the basis of information with respect to the concentration of the microbial particles.

The selectively driving of the one or more air cleaning devices may include performing an air cleaning operation by the air cleaning device when the concentration of the microbial particles is greater than the first preset value.

The selectively driving of the one or more air cleaning devices may include performing an air cleaning operation by the air conditioner or the air cleaner when the concentration of the microbial particles is greater than the first preset value and is less than the second preset value.

The selectively driving of the one or more air cleaning devices may include: driving a ventilator to ventilate the indoor air when the concentration of the microbial particles is greater than the second preset value; and performing the air cleaning operation by the air conditioner or the air cleaner.

In further another embodiments, an air cleaning system includes: a particle separation device suctioning indoor air to separate microbial particles and air particles from the indoor air; a microbial particle passage through which the microbial particles passing through the nozzle part flow; an air particle passage through which remaining particles in the air except for the microbial particles flow; a flow generation device allowing a flow into the microbial particle passage or the air particle passage to be generated; a filter part communicating with the microbial particle passage to collect the microbial particles thereon; a lysis agent supply device supplying a lysis reagent for lysing the microbial particles into the filter part; a luminescence measurement device for detecting an amount or intensity of light emitted from the microbial particles collected onto the filter part; and an air cleaning device operating to clean the air on the basis of concentration of the microbial particles detected by the luminescence measurement device.

The air cleaning device may include an air conditioner in which a microbial elimination unit operating to clean the air when the concentration of the microbial particles is greater than a first preset value and is less than a second preset value is disposed.

The air cleaning device may include: a ventilator operating for a first preset time to ventilate the indoor air when the concentration of the microbial particles is greater than the second preset value; and the air conditioner in which the microbial elimination unit operating to clean the air for a second preset time after the ventilator operates is disposed.

The air cleaning system may further include a display part including a lighting unit displaying colors different from each other depending on the concentration of the microbial particles.

The flow generation device may include: an air pump generating a flow of the microbial particles in the microbial particle passage; and a fan generating a flow of the air particles in the air particle passage.

Advantageous Effects of Invention

According to the air cleaning system and the method of controlling the same, since the concentration of the airborne microbial particles is measured, and at least one of the air cleaning devices is driven according to the measured concentration, it is possible to rapidly actively cope with in response to the degree of the air contamination.

Particularly, when the concentration of the airborne microorganism in the air is low, the air conditioner performs the normal operation. When the concentration of the airborne microorganism is greater than the first preset value, the air cleaning or antibacterial operation may be performed. Also, when the concentration of the airborne microorganism is greater than the second preset value, the ventilating operation and the air cleaning operation may be combined to be performed. Therefore, the operations according to the situations may be easily performed.

The airborne microbial particles in the air may be automatically separated from the air through the virtual impactor structure without manually sampling the airborne microbial particles collected onto the collection plate by the user, and thus the process for separating particles may be easily performed to reduce the time taken to perform the process.

Also, when the separated microbial particles are collected in the collection device or the filter part, the filter part moves toward the luminescence measurement deviceo detect the luminescence amount according to the reaction with the microbial particles, and thus the luminescence amount may be automatically successively measured from the particle separation process to the light emission measurement process.

Here, since the luminous material is applied onto the collection device or the filter part, and the microbial lysis reagent is supplied to the collection device or the filter part, the luminescence measurement process may be easily performed.

Also, the main flow in which the relatively small particles flow and the sub flow in which the relatively large particles flow may be effectively separated from each other by the virtual impactor structure. Also, since the fan is used as the driving part at the main flow side where the pressure loss is relatively low, and the low flow rate pump is used as the driving part at the sub flow side where the pressure loss is relatively high, the airborne microbial measurement apparatus may not increase in volume and weight.

Also, since the display part displaying the information with respect to the microbial concentration on the basis of the light luminescence amount detected in the luminescence measurement device is further provided to display the warning sign when the microbial concentration is higher than the predetermined concentration, the user convenience may increase.

BRIEF DESCRIPTION OF DRAWINGS

FIG. 1 is a perspective view of an airborne microbial measurement apparatus according to an embodiment.

FIG. 2 is a cross-sectional view taken along line I-I' of FIG. 1.

FIG. 3 is a cross-sectional view taken along line II-II' of FIG. 1.

FIG. 4 is a schematic view of inner constitutions of the airborne microbial measurement apparatus according to an embodiment.

FIG. 5 is a schematic view of a nozzle part according to an embodiment.

FIG. 6 is a block diagram of the airborne microbial measurement apparatus according to an embodiment.

FIG. 7 is a flowchart illustrating a method of measuring the airborne microorganism by using the airborne microbial measurement apparatus according to an embodiment.

FIG. 8 is a block diagram of an air cleaning system according to an embodiment.

FIG. 9 is a flowchart illustrating a method of controlling the air cleaning system according to an embodiment.

FIG. 10 is a view of an electric dust collector provided in an airborne microbial measurement apparatus according to a related art.

MODE FOR THE INVENTION

Hereinafter, reference will now be made in detail to the embodiments of the present invention, examples of which are illustrated in the accompanying drawings. The invention may, however, be embodied in many different forms and should not be construed as being limited to the embodiments set forth herein; rather, that alternate embodiments included in other retrogressive inventions or falling within the spirit and scope of the inventive concept will fully convey the concept of the invention to those skilled in the art.

FIG. 1 is a perspective view of an airborne microbial measurement apparatus according to an embodiment, FIG. 2 is a cross-sectional view taken along line I-I' of FIG. 1, and FIG. 3 is a cross-sectional view taken along line II-II' of FIG. 1.

Referring to FIGS. 1 to 3, the airborne microbial measurement apparatus according to an embodiment includes a base 20 and a plurality of devices disposed at an upper side of the base 20. The plurality of devices include a particle separation device 100 for suctioning air to separate airborne microbial particles from the air and a collection device 200 in which the airborne microbial particles separated by the particle separation device 100 are collected.

Also, the plurality of devices may further include a luminescence measurement device 300 disposed at one side of the collection device 200 to detect an amount or intensity of light emitted from the airborne microbial and a control device 400 electrically connected to the luminescence measurement device 300. The control device 400 includes a printed circuit board (PCB) 410 on which a plurality of circuit components are disposed and a display part 420 disposed on the PCB 410 to display information relating to concentration of the airborne microbial particles.

In detail, the particle separation device 100 includes a first housing 110 defining a predetermined inner space and a top surface part 112 coupled to an upper portion of the first housing 110. A plurality of slits 121 are defined in the top surface part 112 as an "air introduction part" into which the air existing outside the particle separation device 100 is suctioned.

The slit 121 may have a width of several mm. Also, since the slit 121 is defined in plurality in the top surface part 112, the air introduced through the slit 121 may have a low resistance, i.e., a low differential pressure between the inside and outside of the slit 121. Thus, the air introduced through the plurality of slits 121 may secure a sufficient flow rate.

A nozzle part 120 through which the air introduced through the slit 121 passes may be provided in the first housing 110. That is, the nozzle part 120 may be disposed in an inner space of the first housing 110. Also, the nozzle part 120 is spaced apart downward from the slit 121 to extend downward.

The nozzle part 120 may be provided in plurality to correspond to the number of the plurality of slits 121. Here, the plurality of the nozzle parts 120 may be spaced apart from each other. Also, the plurality of nozzle part 120 may be disposed at a lower side of the plurality of the slits 121 to correspond to positions of the plurality of slits 121. For example, as illustrated in FIG. 2, the plurality of nozzle parts 120 may be disposed spaced apart from each other in a horizontal direction.

The nozzle part 120 includes an inner passage 125 through which airborne microbial particles in the air introduced into the first housing 110 through the slit 121 flows. The inner passage 125 defines an inner space of the nozzle part 120.

An inlet part 125a defining one end of the nozzle part 120 and through which the airborne microbial is introduced into the inner passage 125 may be defined in the inner passage 125. For example, the inlet part 125a is defined on an upper end of the inner passage 125. The airborne microbial particles in the air introduced through the slit 121 may flow in the inner passage 125 through the inlet part 125a. Air particles from which the airborne microbial particles is separated may flow in an outer space of the inner passage 125 to pass through an air particle passage 129.

Also, an outlet part 125b defining the other end of the nozzle part 120 and through which the airborne microbial particles flowing in the inner passage 125 is discharged from the nozzle part 120. For example, the outlet part 125b is defined on a lower end of the inner passage 125.

A microbial particle passage 127 in which the airborne microbial particles discharged through the outlet part 125b flows may be defined at one side of the outlet part 125b. The air particle passage 129 may be called a first passage or a main flow passage. Also, the microbial particle passage 127 may be celled a second passage or a sub flow passage.

A partition plate 126 for partitioning the air particle passage 129 from the microbial particle passage 127 may be disposed on a lower end of the nozzle part 120. The lower end of the nozzle part 120, i.e., the outlet part 125b may be coupled to the partition plate 126. In detail, a communication hole 126a communicating with the outlet part 125b is defined in the partition plate 126. The communication hole 126a is defined to pass through upper and lower portions of the partition plate 126.

The outlet part 125b is coupled to the communication hole 126a within the partition plate 126. Also, the outlet part 125b may communicate with the microbial particle passage 127 through the communication hole 126a. Since the air particle passage 129 and the microbial particle passage 127 is separated from each other by the partition plate 126, mixture of a particle in the air particle passage 129 and a particle in the microbial particle passage 127 may be prevented.

A second housing 310 in which the luminescence measurement device 300 is disposed is provided at one side of the first housing 110. The microbial particle passage 127 may extend from the partition plate 126 toward the collection device 200. An inner space of the second housing 310 may define at least one portion of the microbial particle passage 127.

A filter case 210 in which a filter part 220 is accommodated and a plurality of filter holes 215 defined in the filter case 210 are provided in the collection device 200. The filter part 220 may be exposed to the outside through the plurality of filter holes 215. Also, the microbial particles flowing through the microbial particle passage 127 may be collected onto the filter part 220 through one of the plurality of filter holes 215.

The plurality of filter holes 215 includes one filter hole communicating with the microbial particle passage 127 and the other filter hole communicating with the microbial particle passage 127 when the filter case 210 rotates. When the other filter hole communicates with the microbial particle passage 127, the one filter hole may face a light receiving device 320.

The filter part 220 may be fixed to an inside of the filter case 210. Also, the filter case 210 may be rotatable.

A filter driving part 250 for providing a rotation force to the filter case 210 is disposed at one side of the filter case 210. For example, the filter driving part 250 may be a motor. A rotation shaft (see reference numeral 255 of FIG. 4) may extend from the filter driving part 250 to the filter case 210.

When the filter driving part 250 is driven, the rotation shaft 255 rotates. Here, the filter case 210 may rotate in a clockwise or counterclockwise direction by the rotation shaft (see reference numeral 255 of FIG. 4). Also, the filter part 220 may rotate together with the filter case 210.

When the filter part 220 is disposed at one position, the one filter hole 215 communicates with the microbial particle passage 127. Thus, the microbial particles flowing through the microbial particle passage 127 may be collected onto the filter part 220 through the one filter hole 215. Here, one area of the filter part 220 in which the microbial particles are collected may correspond to an area that is exposed to the microbial particle passage 127 by the one filter hole 215.

Also, when the filter part 220 rotates, the other filter hole 215 communicates with the microbial particle passage 127. Here, the one filter hole 215 may be disposed at one side of the luminescence measurement device 330.

A pump device 360 driven to flow the microbial particles and a pump connection part 350 extending from the filter case 210 to the pump device 360 are disposed at one side of the collection device 200. The pump device 360 may include an air pump. A portion of the particles in the microbial particle passage 127 except for the microbial particles collected onto the filter part 220, e.g., air particles may flow into the pump device 360 via the pump connection part 350.

The pump connection part 350 includes a cyclone unit 351 of which a flow cross-sectional area is gradually reduced from the filter case 210 toward the pump device 360. The air may increase in flow rate while passing through the cyclone unit 351 and be introduced into the pump device 360.

The pump device 360 may be understood as a device having an advantage over a fan in that the pump device secures a predetermined suction flow rate even though pressure loss occurs. Thus, the pump device 360 may be used to allow a flow of the particles in the microbial particle passage 127 to be generated, thereby improving suction efficiency even though pressure loss occurs in the nozzle part 120 or the filter part 220. Also, since the flow rate of the particles in the microbial particle passage 127 is relatively low, a low-flow rate pump may be applied as the air pump. Therefore, a phenomenon in which the airborne microbial measurement device increases in volume or weight may be prevented.

The luminescence measurement device 300 includes the light receiving part 320 disposed at one side of the collection device 200 to receive the light emitted from the microbial particles. For example, at least one portion of the light receiving part 320 may be disposed in the second housing 310.

When the filter case 210 rotates after the microbial particles are collected onto the filter part 220 through the one filter hole 215, the one filter hole 215 may face the light receiving part 320. The light receiving part 320 may detect an amount or intensity of light emitted from the microbial particles in the filter part 220.

The airborne microbial measurement apparatus 10 may further include a lysis agent supply device 370 for supplying a lysis reagent into the filter part 220 and a supply passage 375 extending from the lysis agent supply device 370 to one filter hole 215 or the filter part 220. The lysis reagent may be understood as a lysis agent for lysing cells (or cell walls) of the airborne microbial particles collected onto the filter part 220. When the cells of the airborne microbial particles react with the lysis reagent, adenosine triphosphate (ATP) is extracted.

Also, a luminous material may be applied onto the filter part 220. The luminous material may be understood as a material for emitting the light by reacting with the ATP of the microbial particles which is extracted by the lysis reagent. The luminous material includes luciferin and luciferase. The luciferin is activated by the ATP existing in the lysed cell to change into active luciferin. The active luciferin is oxidized by the effect of the luciferase that is a luminous enzyme to become oxide luciferin. Here, chemical energy is converted into light energy to emit the light.

The air particle passage 129 through which particles each of which has a relatively small size separated from the airborne microbial particles at an inlet-side of the nozzle part 120, e.g., the air particles flow may be defined in the first housing 110. The particle within the air particle passage 129 may have a size less than that of the particle within the microbial particle passage 127. However, the flow rate in the air particle passage 129 may be greater than that in the microbial particle passage 127.

The air particle passage 129 may be separated from the microbial particle passage 127 by the partition plate 126 to extend toward a blower fan 150. The blower fan 150 is a device for allowing a flow into the air particle passage 129 to be generated. For example, the blower fan 150 may be accommodated within a fan housing 155. The fan housing 155 is disposed on a lower portion of the first housing 110.

Also, the blower fan 150 may be understood as a device that is capable of securing a sufficient flow rate when the pressure loss is low when compared to the air pump. Thus, the blower fan 150 is provided in a passage where the pressure loss is low such as the air particle passage 129 to allow a sufficient air particle flow to be generated (main flow). The pump device 360 may be called "flow generation device" together with the blower fan 150.

FIG. 4 is a schematic view of inner constitutions of the airborne microbial measurement apparatus according to an embodiment, and FIG. 5 is a schematic view of a nozzle part according to an embodiment. An operation of the airborne microbial measurement apparatus according to an embodiment will be simply described with reference to FIGS. 4 and 5.

When the pump device 360 and the blower fan 150 are driven, the air (see reference symbol A of FIG. 5) existing outside the airborne microbial measurement apparatus 10 is introduced into the first housing 110 through the plurality of slits 121 in the top surface part 112.

The air may increase in flow rate while passing through the plurality of slits 121 due to the narrow cross-sectional area of the passage. The airborne microbial particles having relatively large sizes in the air passing through the plurality of slits 121 may be introduced into the inner passage 125 through the inlet part 125*a* of the nozzle part 120 (see reference symbol C of FIG. 5). Also, the airborne microbial particles may be discharged from the inner passage 125 trough the outlet part 125*b* to flow the microbial particle passage 127 through the communication hole 126*a* of the partition plate 126.

On the other hand, the air particles having relatively small sizes in the air passing through the plurality of slits 121 may be changed in traveling direction (see reference symbol B of FIG. 5). Thus, the air particles does not flow into the inner passage 125 but flow along the outer space of the nozzle part 120. Also, the air particles flow through the air particle passage 129 to pass through the blower fan 150. As described above, the flow rate of the air particles may be greater than that of the microbial particles.

That is, in the process in which the air flows through the nozzle having the narrow cross-section, the airborne microbial particle having a relatively large size may be introduced into the inner passage 125 through the inlet part 125*a*. Also, the air particle having a relatively small size may be changed in traveling direction to flow in a stream line through a space between the slit 121 and the inlet part 125*a*, thereby flowing through the air particle passage 129.

The particle separation structure may be called a virtual impactor structure. In the current embodiment, since the virtual impactor structure is applied, the airborne microbial particles may be easily separated from the air particles.

The airborne microbial particles flowing through the microbial particle passage 127 may flow into the collection device 200 and be collected on the one area of the filter part 220 via the one filter hole 215 of the filter case 210.

This collection process is performed during a preset time, and then the lysis reagent is supplied from the lysis agent supply device 370 into the filter part 220. The microbial particles collected onto the filter part 220 may be lysed by the lysis reagent to extract the ATP, thereby reacting with the luminous material applied onto the filter part 220.

Also, the filter driving part 250 is driven to rotate the filter case 210. Thus, the one filter hole 215 is disposed at one side of the luminescence measurement device 300 to face the light receiving part 320, and the other filter hole 215 is disposed to communicate with the microbial particle passage 127. Therefore, when the next collection process is performed, the microbial particles flowing through the microbial particle passage 127 may be collected on the other area of the filter part 220 via the other filter hole 215 of the filter case 210.

Like this, by the driving of the filter driving part 250, the one area of the filter part 220 in which the microbial particles are collected moves to face the luminescence measurement device 300 or the light receiving part 320, and the other area of the filter part 220 moves to a position where the filter part 220 communicates with the microbial particle passage 127 to collect the microbial particles. Thus, since the filter case 210 and the filter part 220 are rotatable, the microbial collection process and the luminescence process may be automatically conducted.

When the ATP reacts with the luminous material, predetermined light may be emitted. Here, the light receiving part 320 may detect the amount or intensity of the emitted light.

FIG. 6 is a block diagram of the airborne microbial measurement apparatus according to an embodiment, and FIG. 7 is a flowchart illustrating a method of measuring the airborne microorganism by using the airborne microbial measurement apparatus according to an embodiment.

Referring to FIG. 6, the airborne microbial measurement apparatus 10 according to an embodiment includes the pump device 360 allowing the flow of the airborne microbial particles to be generated and the blower fan 150 allowing the flow of the air particles to be generated.

Also, the airborne microbial measurement apparatus 10 may further include the filter driving part 250 for rotating the filter case 210 and the filter part 220 and the lysis agent supply device 370 for supplying lysis reagent into the filter 220.

The airborne microbial measurement apparatus 10 includes the display part 420 on which information with respect to concentration of the airborne microbial particles collected onto the filter part 220. The display part 420 may include a lighting unit displayed with different colors depending on concentration values of the airborne microbial particles. For example, the lighting unit may include a first lighting part displayed with a green color when the airborne microbial particles have a low concentration value, a second lighting part displayed with a yellow color when the airborne microbial particles have a middle concentration value, and a third lighting part displayed with a red color when the airborne microbial particles have a high concentration value. For another example, the first to third lighting units may be provided as one lighting part.

The airborne microbial measurement apparatus 10 includes the light receiving part 320 detecting the amount of light emitted from the microbial particles collected onto the filter part 220 and a timer 460 integrating an elapsing time in the process for collecting the microbial particles and the process for supplying the lysis reagent.

Information detected by the light receiving part 320 or the timer 460 may be transmitted to the control part 450. The control part 450 may control of operations of the pump device 360, the blower fan 150, the filter driving part 250, the lysis agent supply device 370, and the display part 420 on the basis of the transmitted information.

Referring to FIG. 7, when the airborne microbial measurement apparatus 10 is turned on to operate the blower fan 150 and the pump device 360, the air outside the airborne microbial measurement apparatus 10 may be introduced into the first housing 110 through the plurality of slits 121. Also, the airborne microbial particles may be separated from the air particles to respectively flow in the microbial particle passage 127 and the air particle passage 129 by the virtual impactor structure within the first housing 110. In operations S11 and S12, the particles flowing through the microbial particle passage 127 may be collected onto the filter part 220.

This collecting process may be performed during a first preset time. In operation S13, the elapsing time is integrated by the timer 460, and the control part 450 recognizes whether the first preset time elapses.

When the first preset time elapses, the blower fan 150 and the pump device 360 stop driving. Then, the lysis agent supply device 370 operates to supply the lysis reagent into the filter part 220. The lysis reagent is supplied into the filter part 220 during a second preset time. When the second present time elapses, the lysis agent supply device 370 stops operating. In operations S14 and S15, the lysis reagent may lyses the microbial particles collected onto the filter part 220 to extract the ATP, and the extracted ATP reacts with the luminous material applied onto the filter part 220 to emit predetermined light.

The filter driving part 250 operates. When the filter driving part 250 operates, the filter case 210 and the filter part 220 move so that the one area of the filter part 220 onto which the microbial particles are collected is disposed at one side of the luminescence measurement device 300. Thus, the one area of the filter part 220 may face the light receiving part 320. Also, in operation S16, the other area of the filter part 220 may be disposed to communicate with the microbial particle passage 127.

The luminescence measurement device 300 operates, and the light receiving part 320 detects the amount or intensity of the light emitted from the filter part 220. The amount of intensity of the light may be proportional to the microbial concentration. That is, when the light has a great amount or intensity, it may be recognized that the microbial concentration is high in proportional to the great amount or intensity of the light. Also, when the light has a small amount or intensity, it may be recognized that the microbial concentration is low in proportional to the small amount or intensity of the light.

The control part 450 may display information relating to the microbial concentration on the display part 420 on the basis of the information with respect to the amount or intensity of the light transmitted from the light receiving part 320. For example, in operations S17 and S18, the different colors of lighting parts may be activated in the display part 420.

Like this, since the process for collecting the microbial particles and the luminescence measurement process are automatically and successively performed, the airborne microbial measurement process may be easily conducted. Also, since the information relating to the microbial concentration is displayed on the display part, a user may easily recognize the airborne microbial concentration.

FIG. 8 is a block diagram of an air cleaning system according to an embodiment.

Referring to FIG. 8, an air cleaning system 1 according to an embodiment includes the airborne microbial measurement apparatus 10 and a plurality of air cleaning devices 500, 600, and 700 for conditioning the air on the basis of information with respect to the concentration of the airborne microorganism or a degree of air contamination detected by the airborne microbial measurement apparatus 10.

The airborne microbial measurement apparatus 10 includes the light receiving part 320 detecting the concentration of the airborne microorganism and the control part 450 controlling the display part 420 so that the display part 420 displays the information with respect to the microbial concentration or the degree of air contamination on the basis of the information detected by the light receiving part 320. Also, the airborne microbial measurement apparatus 10 may further include a first communication part 480 that communicates with the plurality of the air cleaning devices 500, 600, and 700.

When at least one of the plurality of the air cleaning devices 500, 600, and 700 needs to be driven on the basis of the microbial concentration detected by the airborne microbial measurement apparatus 10, the control part 450 may transmit an operation command to the at least one air cleaning device through the first communication part 480.

The plurality of air cleaning devices 500, 600, and 700 include an air conditioner 500 that performs a normal operation such as a cooling or heating operation for an indoor space and an air conditioning operation, an air cleaner 600 suctioning contaminated air and filtering or antibacterial treating the suctioned air to discharge the filtered or antibacterial treated air, and a ventilator 700 for replacing contaminated indoor air with clean outdoor air.

The air conditioner 500 and the air cleaner 600 respectively include microbial elimination units 550 and 650. For example, each of the microbial elimination units 550 and 650 includes a filter member for filtering the microbial particles in the air or an ion generators generating ions to remove the microorganism in the air, e.g., a virus or a bacteria. Also, an antibacterial material may be applied onto the filter member. The microbial elimination unit 550 of the air conditioner 500 may be called a "first microbial elimination unit", and the microbial elimination unit 600 of the air cleaner 600 may be called a "second microbial elimination unit".

The air cleaning system 1 may further include one or more communication parts 580, 680, and 780 that are communicably connected to the first communication part 480. The communication parts 580, 680, and 700 include a second communication part 580 disposed in the air conditioner 500, a third communication part 680 disposed in the air cleaner 600, and a fourth communication part 780 disposed in the ventilator 700. Each of the communication parts 580, 680, and 700 may receive a driving command from the first communication part 480 to transmit the received driving command to the air cleaning devices 500, 600, and 700.

Although a separate communication part is disposed in each of the air cleaning devices in FIG. 8, alternatively, one communication module may be connected to the first communication part 480, and a predetermined command may be transmitted from the one communication module to each of the plurality of air cleaning devices 500, 600, and 700.

As shown in Table 1 below, the plurality of air cleaning devices 500, 600, and 700 may selectively operate or be combined with each other to operate according to the concentration of the microorganism in the air or the degree of air contamination.

TABLE 1

| Microbial concentration (degree of air contamination) | When operate in normal mode of air conditioner | When not operate air conditioner |
|---|---|---|
| First preset value or less | Perform cooling/heating operation of air conditioner | Not perform operation of air cleaner |
| First preset value to second preset value | Perform air cleaning operation of air conditioner | Perform air cleaning operation of air cleaner |
| Second preset value or more | Perform operations of ventilator and air conditioner | Perform operations of ventilator and air cleaner |

As shown in Table 1 above, when the microbial concentration detected by the airborne microbial measurement apparatus 10 is less than the first preset value, it is recognized that the degree of air contamination is in a range in which it is unnecessary to perform the air cleaning operation. That is, the first preset value corresponds to a boundary value for determining whether or not to perform the air cleaning operation.

Thus, when the air conditioner 500 performs the normal mode operation (the cooling or heating operation), only the cooling or heating operation is performed without performing a separate air cleaning operation. Also, when the air conditioner 500 does not operate, the separate air cleaning operation is not performed.

On the other hand, when the microbial concentration detected by the airborne microbial measurement apparatus 10 is greater than the first preset value and less than the second preset value, the degree of air contamination corresponds to a middle contamination level. Thus, it is recognized that the degree of air contamination is in a range in which the it is necessary to perform the air cleaning operation by one air cleaning device.

Thus, when the air conditioner 500 performs the normal mode operation (the cooling or heating operation), the air conditioner 500 performs the air cleaning operation together with the cooling or heating operation. That is, the air may pass through the filter member or ion generator disposed in the air conditioner 500.

On the other hand, when the air conditioner 500 does not operate, the air cleaner 600 may perform the air cleaning operation instead of the air conditioner 500 which has a relatively large amount of power consumption. That is, the air may pass through the filter member or ion generator disposed in the air cleaner 600.

Also, when the microbial concentration detected by the airborne microbial measurement apparatus 10 is greater than the second preset value, the degree of air contamination corresponds to a high contamination level. Thus, it is recognized that it is necessary to perform a combined operation by the plurality of air cleaning devices.

Thus, when the air conditioner 500 performs the normal mode operation (the cooling or heating operation), the ventilator 700 ventilates the indoor air, and the air conditioner 500 performs the air cleaning operation together with the cooling or heating operation. For example, the ventilator 700 operates to ventilate the indoor air for the first preset time, and then the air conditioner 500 performs the air cleaning operation for the second preset time.

On the other hand, when the air conditioner 500 does not operate, the ventilator 700 ventilates the indoor air, and the air cleaner 600 performs the air cleaning operation. For example, the ventilator 700 operates to ventilate the indoor air for the first preset time, and then the air cleaner 600 performs the air cleaning operation for the second preset time.

FIG. 9 is a flowchart illustrating a method of controlling the air cleaning system according to an embodiment.

Referring to FIG. 9, a process of collecting the microbial particles by using the airborne microbial measurement apparatus 10 according to an embodiment is performed. That is, when the blower fan 150 and the pump unit 350 are driven, the indoor air is introduced into the first housing 110 through the plurality of slits 121. Here, the microbial particles in the indoor air may be collected onto the filter part 220 via the microbial particle passage 127. Also, in operation S21, the air particles in the indoor air, from which the microbial particles are separated, may flow into the blower fan 150 via the air particle passage 129.

In operation S22, the microbial particles collected onto the filter part 220 is lysed by the lysis reagent supplied from the lysis agent supply device 370 to extract the ATP, and the extracted ATP reacts with the luminous material.

A predetermined light is emitted from the filter part 220 by the reaction between the ATP and the luminous material. The luminescence measurement device 300 may detect the amount or intensity of the light. In operations S23 and S24, the contamination of microbial particles in the air may be recognized on the basis of the amount or intensity of the detected light.

The concentration of the microbial particles may correspond to the degree of air contamination. The plurality of air cleaning devices 500, 600, and 700 may operate according to whether the microbial contamination is greater than the preset value. In detail, it is recognized whether the concentration of the microbial particles is less than the first preset value. The first preset value may be understood as a threshold value for determining whether or not to perform an operation of at least one of the plurality of air cleaning devices 500, 600, and 700.

When the concentration of the microbial particles is less than the first preset value, it is recognized that the concentration of the microbial particles or the degree of the indoor air contamination is in an allowable range. Thus, the air conditioner 500 may perform the normal operation. The normal operation represents the cooling or heating operation of the air conditioner 500. That is, the first preset value may be understood as a threshold limit value of the air conditioning operation. However, when it is unnecessary to perform the normal operation of the air conditioner 500, the air conditioner 500 may not operate (see the Non-operating time of the air conditioner of the air conditioner)

Information representing that the indoor air is relatively clean may be displayed on the display part 420. For example, in operations S26 and S27, green light may be displayed through the lighting unit disposed in the display part 420.

In operation S28, when the concentration of the microbial particles is greater than the first preset value and less than the second preset value, the concentration of the microbial particles is slightly high, and thus it is recognized that the degree of indoor air contamination is slightly high.

Here, the air conditioning operation or an antibacterial operation may be performed by the air conditioner 500 or the air cleaner 600. Here, the air conditioning or antibacterial operation may be understood that the first and second microbial elimination units 550 and 650 respectively disposed in the air conditioner 500 and the air cleaner 600, e.g., the filter member or the ion generator acts on the air.

For example, when the air conditioner 500 performs the cooling or heating operation, the air conditioning or antibacterial operation may be performed through the air conditioner 500. On the other hand, when the air conditioner 500 does not operate, the air conditioning or antibacterial operation may be performed through the air cleaner 600.

Information representing that the indoor air is relatively contaminated may be displayed on the display part 420. For example, in operation S29, orange light may be displayed through the lighting unit disposed in the display part 420.

As a result of the operation S28, in operation S30, when it is recognized that the concentration of the microbial particles is greater than the second preset value, the concentration of the microbial particles is very high, and thus it is recognized that the degree of the indoor contamination is slightly high.

Here, the air conditioner 500 or the air cleaner 600 may operate together with the ventilator 700. For example, while the air conditioner 500 performs the cooling or heating operation, the ventilator 700 may operate to ventilate the indoor air. Also, the air cleaning or antibacterial operation may be performed through the air conditioner 500.

On the other hand, when the air conditioner 500 does not operate, the ventilator 700 may operate to ventilate the indoor air. Also, the air cleaning or antibacterial operation may be performed through the air cleaner 600.

Information representing that the degree of the contamination of the indoor air is high may be displayed on the display part 420. For example, in operation S31, red light may be displayed through the lighting unit disposed in the display part 420.

Like this, the airborne microbial measurement apparatus may easily measure the contamination of the microbial particles in the indoor air in real time, and also at least one of the plurality of air cleaning devices may selectively operate on the basis of the measured microbial concentration. Therefore, according to the air cleaning system, the contaminated air may be effectively cleaned.

INDUSTRIAL APPLICABILITY

According to the air cleaning system and the method of controlling the same, since the concentration of the airborne microbial particles is measured, and at least one of the air cleaning devices is driven according to the measured concentration, it is possible to rapidly actively cope with according to the degree of the air contamination. Therefore, industrial applicability is significantly high.

The invention claimed is:

1. An air cleaning system comprising:
a particle separation device for suctioning indoor air to separate microbial particles from air particles;
a microbial particle passage through which the microbial particles separated at the particle separation device flow;
an air particle passage through which remaining particles in the air except for the microbial particles flow;
a partition plate for partitioning the air particle passage from the microbial particle passage;
a collection device collecting the microbial particles separated by the particle separation device;
a luminescence measurement device for detecting an amount or intensity of light emitted from the microbial particles collected in the collection device; and
at least one air cleaning device that selectively operates on the basis of contamination of the microbial particles detected by the luminescence measurement device.

2. The air cleaning system according to claim 1, wherein the air cleaning device comprises at least one of:
an air conditioner for cooling or heating an indoor space and cleaning the indoor air;
an air cleaner for cleaning the indoor air; and
a ventilator for ventilating the indoor space by exchanging the indoor air with outdoor air.

3. The air cleaning system according to claim 2, wherein, in the air conditioner or the air cleaner, a filter member for filtering the microbial particles or an ion generator for generating ions to eliminate the microbial particles is disposed to perform the indoor air cleaning operation.

4. The air cleaning system according to claim 3, wherein, when the concentration of the microbial particles is greater than a preset value, one of the air conditioner and the air cleaner performs the indoor air cleaning operation.

5. The air cleaning system according to claim 4, wherein, when the concentration of the microbial particles is in ranging from the first preset value to a second preset value, while the air conditioner operates, the air conditioner performs the indoor air cleaning operation, and when the air conditioner does not operate, the air cleaner performs the indoor air cleaning operation.

6. The air cleaning system according to claim 5, wherein, when the concentration of the microbial particles is greater than a second preset value, while the air conditioner operates, the ventilator operates, and the air conditioner performs the indoor air cleaning operation, and when the air conditioner does not operate, the ventilator operates, and the air cleaner performs the indoor air cleaning operation.

7. The air cleaning system according to claim 1, wherein the particle separation device further comprises:
a pump for generating a flow of the microbial particles; and
a blower fan for generating a flow of the air particles.

8. The air cleaning system according to claim 1, wherein the particle separation device comprises:
an introduction part for introducing the indoor air; and
a nozzle part disposed at one side of the introduction part, wherein the nozzle part comprises:
an inlet spaced apart from the introduction part in one direction to introduce the microbial particles; and
an outlet discharging the microbial particles toward the collection device.

9. The air cleaning system according to claim 1, wherein the collection device comprises:
a filter part for collecting the microbial particles;
a filter case accommodating the filter part; and
a plurality of filter holes defined in the filter case to communicate with a microbial particle passage.

10. The air cleaning system according to claim 9, further comprises a filter driving part for rotating the filter part or the filter case, wherein, when the filter driving part operates in the state where the microbial particles are collected onto the filter part through one of the plurality of filter holes, the other one of the plurality of filter holes moves to a position where the microbial particles are collectible.

11. The air cleaning system according to claim 1, further comprises:
a lysis agent supply device for supplying lysis reagent into the filter part; and
a luminous material disposed in the filter part.

12. A method of controlling an air cleaning system according to claim 1, the method comprising:
separating microbial particles and air particles from indoor air;
collecting the separated microbial particles onto a filter part;
supplying a lysis reagent into the filter part to extract adenosine triphosphate (ATP) of the microbial particles, wherein the extracted ATP reacts with a luminous material;
detecting an amount or intensity of light emitted by the reaction to recognize concentration of the microbial particles; and
selectively driving one or more air cleaning devices on the basis of information with respect to the concentration of the microbial particles.

13. The method according to claim 12, wherein the selectively driving of the one or more air cleaning devices comprises performing an air cleaning operation by the air cleaning device when the concentration of the microbial particles is greater than the first preset value.

14. The method according to claim 13, wherein the selectively driving of the one or more air cleaning devices comprises performing an air cleaning operation by the air conditioner or the air cleaner when the concentration of the microbial particles is greater than the first preset value and is less than the second preset value.

15. The method according to claim 14, wherein the selectively driving of the one or more air cleaning devices comprises:
   driving a ventilator to ventilate the indoor air when the concentration of the microbial particles is greater than the second preset value; and
   performing the air cleaning operation by the air conditioner or the air cleaner.

16. An air cleaning system comprising:
   a particle separation device suctioning indoor air to separate microbial particles and air particles from the indoor air;
   a microbial particle passage through which the microbial particles separated at the particle separation device flow;
   an air particle passage through which remaining particles in the air except for the microbial particles flow;
   a flow generation device allowing a flow into the microbial particle passage or the air particle passage to be generated;
   a filter part communicating with the microbial particle passage to collect the microbial particles thereon;
   a lysis agent supply device supplying a lysis reagent for lysing the microbial particles into the filter part;
   a luminescence measurement device for detecting an amount or intensity of light emitted from the microbial particles collected onto the filter part; and
   an air cleaning device operating to clean the air on the basis of concentration of the microbial particles detected by the luminescence measurement device.

17. The air cleaning system according to claim 16, wherein the air cleaning device comprises an air conditioner in which a microbial elimination unit operating to clean the air when the concentration of the microbial particles is greater than a first preset value and is less than a second preset value is disposed.

18. The air cleaning system according to claim 17, further comprising a ventilator operating for a first preset time to ventilate the indoor air when the concentration of the microbial particles is greater than the second preset value; and wherein the air conditioner operates to clean the air for a second preset time after the ventilator operates.

19. The air cleaning system according to claim 16, further comprising a display part comprising a lighting unit displaying colors different from each other depending on the concentration of the microbial particles.

20. The air cleaning system according to claim 16, wherein the flow generation device comprises:
   an air pump generating a flow of the microbial particles in the microbial particle passage; and
   a fan generating a flow of the air particles in the air particle passage.

\* \* \* \* \*